(12) United States Patent
Andrews, Jr.

(10) Patent No.: US 10,663,402 B2
(45) Date of Patent: May 26, 2020

(54) APPARATUS AND METHOD FOR MEASURING FREE WATER IN HYDROCARBON FUELS AND METHOD OF CALIBRATING THE APPARATUS

(71) Applicant: Telectro-Mek, Inc., Fort Wayne, IN (US)

(72) Inventor: James Edward Andrews, Jr., Fort Wayne, IN (US)

(73) Assignee: Telectro-Mek, Inc., Fort Wayne, IN (US)

( * ) Notice: Subject to any disclaimer, the term of this patent is extended or adjusted under 35 U.S.C. 154(b) by 180 days.

(21) Appl. No.: 15/830,042

(22) Filed: Dec. 4, 2017

(65) Prior Publication Data

US 2019/0170643 A1    Jun. 6, 2019

(51) Int. Cl.
   *G01N 21/64* (2006.01)
   *G01N 33/28* (2006.01)
   *G01N 21/77* (2006.01)

(52) U.S. Cl.
   CPC ......... *G01N 21/643* (2013.01); *G01N 21/645* (2013.01); *G01N 21/77* (2013.01); *G01N 33/2847* (2013.01); *G01N 2021/6439* (2013.01); *G01N 2021/7786* (2013.01); *G01N 2201/062* (2013.01)

(58) Field of Classification Search
   CPC ... G01N 2021/6439; G01N 2021/7786; G01N 21/64; G01N 21/643; G01N 21/645; G01N 21/77; G01N 2201/062; G01N 33/2847

USPC ............. 436/39, 40, 60, 164, 165, 169, 172; 422/401, 402, 420, 82.05, 82.08, 534
See application file for complete search history.

(56) References Cited

U.S. PATENT DOCUMENTS

| | | | |
|---|---|---|---|
| 2,844,025 A * | 7/1958 | Ruskin | G01N 31/222 436/39 |
| 3,063,289 A | 11/1961 | Moul | |
| 3,066,221 A * | 11/1962 | Thyrum | G01N 21/64 250/459.1 |
| 3,308,649 A | 3/1967 | Colechia | |
| 3,341,298 A * | 9/1967 | Pietrangelo | G01N 31/22 436/40 |
| 3,500,046 A * | 3/1970 | Caldwell | G01N 21/64 250/365 |
| 3,614,433 A | 10/1971 | Caldwell | |
| 4,044,604 A | 8/1977 | Russ | |
| 4,045,139 A | 8/1977 | Russ | |
| 4,193,694 A | 3/1980 | Smith | |

(Continued)

*Primary Examiner* — Maureen Wallenhorst
(74) *Attorney, Agent, or Firm* — George Pappas

(57) ABSTRACT

An apparatus and method of measuring free water, also known as undissolved water, in hydrocarbon fuel. A housing defines a chamber and is adapted to receive a fluorescein impregnated filter pad in the chamber between a UV light source and a light sensor. The filter pad is exposed to the fuel causing the free water to react with the fluorescein and is then placed within the chamber between the light source and sensor. The UV light strikes one side surface of the filter pad and excites the reacted fluorescein thereby causing light emitted from the UV light reacted fluorescein filter pad opposite side surface to strike the light sensor. An output from the light sensor is proportional to the fluorescein on the filter pad which reacted with free water and is used for providing an output value representative of the free water present in the hydrocarbon fuel.

20 Claims, 13 Drawing Sheets

(56) References Cited

U.S. PATENT DOCUMENTS

| | | |
|---|---|---|
| 5,200,064 A | 4/1993 | Russ |
| 5,576,482 A | 11/1996 | Russ et al. |
| 6,064,480 A | 5/2000 | Mountain et al. |
| 7,518,719 B2 | 4/2009 | Sprenger et al. |
| 7,846,390 B2 | 12/2010 | Hegazi |
| 7,889,337 B2 | 2/2011 | Al-Jaroudi et al. |
| 8,045,154 B2 | 10/2011 | Hegazi |
| 8,149,401 B2 | 4/2012 | Stevens et al. |
| 8,263,000 B2 | 9/2012 | Hegazi |
| 2012/0210769 A1 | 8/2012 | Roper |
| 2014/0273051 A1* | 9/2014 | Reddy .................... G01N 21/78 435/25 |
| 2015/0090012 A1 | 4/2015 | Fougere |
| 2015/0093833 A1 | 4/2015 | Fougere |
| 2015/0168368 A1* | 6/2015 | Hegazi .................... G01N 21/64 73/61.48 |

* cited by examiner

APPARATUS AND METHOD FOR MEASURING FREE WATER IN HYDROCARBON FUELS AND METHOD OF CALIBRATING THE APPARATUS

BACKGROUND OF THE INVENTION

1. Field of the Invention

The present invention relates to the technical field of measuring free/undissolved water in hydrocarbon fuels. More particularly, the present invention relates to an apparatus and method for measuring free water in hydrocarbon fuel, such as aviation diesel fuel, and a method of calibrating the apparatus. The apparatus and method can be used for determining whether the fuel contains sufficiently low levels of free water for efficient and safe use in hydrocarbon engines.

2. Background

Determining acceptable "free water", also known as "undissolved water" levels in hydrocarbon fuels is important so as to assure hydrocarbon engines which operate with such fuel run efficiently and without malfunction. As can be appreciated, this is of utmost importance in aviation equipment and engines, such as jet engines.

Apparatus for determining free water contamination levels are known as, for example, shown and described in U.S. Pat. Nos. 5,200,064 and 5,576,482. In these prior apparatus, a desired volume of fuel to be tested is passed through a fluorescein impregnated paper filter. The filters are typically flat/thin and disk shaped, and are sometimes referred to as "filter pads" in the industry. Free water that may be present in the fuel comes in contact with the fluorescein as the fuel and free water travel through the filter pad thereby causing the fluorescein on the filter to react in a known and customary manner. Essentially, the water reacted fluorescein changes color and fluoresces/emits light in the presence of ultra violet (UV) light. UV light is then directed onto the fuel exposed test filter and the fluorescing light reflecting back from the test filter is used to determine the free water contamination level in the fuel.

In some prior apparatus, the fluorescing light reflecting back from the fuel exposed test filter is visually compared to the reflected light of sample filters of known free water exposure. The free water contamination level is thereby determined by selecting the sample filter which most closely resembles the appearance of the fuel exposed test filter.

In other prior apparatus, the fluorescing light reflecting back from the fuel exposed test filter is measured with a light/photo sensor. In these apparatus, light reflecting back from an unexposed filter is first measured with the light/photo sensor. The fuel to be tested is then passed through that same filter. A second light/photo sensor measurement is then obtained of the fluorescing light reflecting back from the fuel exposed test filter. The unexposed filter/first measurement is then compared with the exposed filter/second measurement and that differential is used for determining the fuel free water contamination level. In apparatus of this character, a plastic yellow filter is positioned between the filter pad and the light/photo sensor (in the path of the reflecting fluorescing light to the sensor) while still allowing UV light from the UV light source to travel to the filter pad. The yellow filter thus helps filter/prevent UV light which is traveling from the UV light source to the filter pad from reaching the light/photo sensor.

Although the prior apparatus and methods provide reasonably reliable means for determining acceptable free water contamination levels, they leave room for human error and inaccuracies. Visually inspecting and comparing the fuel exposed test filters with sample filters of known free water exposure can obviously lead to human error and inaccuracies.

In the apparatus using light/photo sensors, although a yellow filter is used to help block UV light from reaching the sensor, it has been found that unacceptable amounts of UV and other light can still reach the sensor thereby causing inaccuracies. Moreover, the differential value obtained between the pre and post exposed test filter measurements must still be compared to known differential values of free water exposure filter pads and, it has been found that, depending on how the known differential values were obtained relative to the subject actual test filter measurements, the resulting conclusion/determination regarding the free water contamination level of the tested fuel can be inaccurate.

Further yet, it has been found that not all of the free water in the fuel being tested is actually delivered to the filter pad, thereby leading to yet more inaccuracies. This is because some of the free water in the fuel will cling to the walls of the vessel containing the fuel to be tested and/or will cling to the tubing/piping leading from the vessel to the filter pad. Also, the velocity at which the fuel is delivered through the filter pad will cause a variance in the amount of fluorescein which comes in contact with and reacts with the free water. Hence, it has been found that, depending on the material and shape of the vessel containing the test fuel, the material and shape of tubing/piping from the vessel to the filter pad, the velocity at which the test fuel travels through the filter pad, etc., hereinafter "delivery collection method", the amount of free water in the test fuel that actually reaches the filter pad and which reacts with the fluorescein varies and leads to yet more inaccuracies.

Accordingly there is a need for an improved more accurate and reliable free water measuring apparatus and method for determining acceptable free water contamination levels in hydrocarbon fuels.

SUMMARY OF THE INVENTION

The present invention overcomes the above discussed and other disadvantageous and inaccuracies of prior apparatus and methods for measuring free water in hydrocarbon fuel which are used for determining whether the fuel contains acceptable sufficiently low levels of free water for efficient and safe use in hydrocarbon engines.

In one form thereof, the present invention is directed to an apparatus and method for measuring free water in hydrocarbon fuel. The apparatus includes an elongate housing defining opposing terminal ends. A UV light source, preferably a 405 nm UV light emitting diode (UV LED), is provided at the one terminal end of the housing. A light sensor, preferably a silicon photovoltaic diode detector (Si PV Detector), is provided at the other terminal end of the housing. A generally flat fluorescein impregnated filter pad having opposing generally flat surfaces is selectively located in the housing between the UV light source and the light sensor whereby one of the filter pad surfaces faces the UV light source, the other opposing side surface of the filter pad faces the light sensor, and UV light is blocked and/or cannot directly travel from the UV light source directly to the light sensor without traveling through the filter pad.

In operation, filter pad which has been exposed to a test volume of the hydrocarbon fuel by passing the fuel through the filter pad is selectively located in the housing between the UV light source and the light sensor. One of the filter pad flat side surfaces is coated/impregnated with fluorescein. The filter pad is located in the housing with the fluorescein coated side surface facing the light sensor and the uncoated side surface facing the UV light source. The filter pad is preferably made of paper and is translucent whereby the UV light striking the uncoated surface causes the fluorescein on the filter pad opposite/coated side surface which reacted with free water to fluoresce and emit light. Accordingly, fluorescing light/photons from the reacted fluorescein on the filter pad coated side surface is transmitted towards and travels to the sensor. The filter pad hence helps block UV light from traveling from the UV light source directly to the light sensor while utilizing the UV light being transmitted through the filter membrane for exciting the reacted fluorescein. The output from the light sensor is consequently not or is only negligibly influenced by UV light and is a more accurate measurement of the reacted fluorescein. The output from the light sensor is proportional to the fluorescein on the filter pad which reacted with free water and is then used for determining the free water in the hydrocarbon fuel and determining whether or not the tested fuel contains a sufficiently low/acceptable free water level.

More particularly, the light sensor electrical output is thereafter converted to a digital signal which is further processed as may be needed or required by a microprocessor. The microprocessor then displays a numeric value (hereinafter apparatus or device "output value") representative of the free water present in the tested fuel.

So as to increase accuracy and prevent UV and/or other unwanted light from negatively influencing the accuracy of the light sensor output, a UV optical filter/lens can be provided between the UV light source and the filter pad for blocking impure sideband transmissions and allowing primarily only the desired UV light bandwidth to travel from the UV light source to the filter pad. Preferably, the UV optical filter is a 300 to 500 nm, and most preferably is a 400 nm, bandpass optical filter. Additionally, one or more and preferably two fluorescing light optical filters/lenses can be provided between the filter pad and the light sensor for similarly blocking impure sideband transmissions and allowing primarily only the desired fluorescing light/photon bandwidth to travel from the filter pad to the light sensor. Preferably, the fluorescing light optical filters are 500 to 650 nm, and most preferably are 550 nm, bandpass optical filters.

So as to further increase accuracy and reliability of apparatus as described above and/or other filter pad reading devices which measure free water in hydrocarbon fuel (hereinafter collectively "filter pad reading devices"), in another form thereof, the present invention is directed to an filter pad reading device which includes a housing, a UV light source and a plurality of light sensors. The housing is adapted to selectively receive a fluorescein impregnated filter pad which has been exposed to a test volume of the hydrocarbon fuel by passing the fuel therethrough. The housing if further adapted to allow UV light to be directed onto the filter pad and for fluorescing light from the filter pad emitted by the fluorescein which reacted with water to travel to each of the light sensors. The outputs from each of the plurality of light sensors are averaged for providing the filter pad reading device output value.

So as to yet further increase accuracy and reliability of filter pad reading devices for measuring free water in hydrocarbon fuel, in yet another form thereof, the present invention is directed to a filter pad reading device which includes a housing, a UV light source and a digital camera capable of providing a digital image output. The housing is adapted to selectively receive a fluorescein impregnated filter pad which has been exposed to a test volume of the hydrocarbon fuel by passing the fuel therethrough. The housing if further adapted to allow UV light to be directed onto the filter pad and for fluorescing light from the filter pad emitted by the fluorescein which reacted with water to travel to the digital camera. The digital image output from the camera is divided into pixel areas and/or individual pixels and each of the pixel areas or pixels are assigned a weighted value proportional to the fluorescing light received at that pixel area or pixel. The weighted values are then averaged for providing the filter pad reading device output value.

In another form thereof, the present invention is directed to a method of measuring free water in hydrocarbon fuel which includes the steps of: providing a housing which includes a UV light source and a light sensor and defines a chamber between the UV light source and the light sensor; exposing the hydrocarbon fuel to a fluorescein impregnated filter pad having opposing side surfaces thereby causing free water in the fuel to react with the fluorescein on the filter pad; placing the filter pad in the chamber between the UV light source and the light sensor thereby causing UV light from the UV light source to strike one side surface of the filter pad and excite the reacted fluorescein, and causing light emitted from the UV light reacted fluorescein filter pad opposite side surface to strike the light sensor; and, using an output from the light sensor provide an output value representative of the free water present in the hydrocarbon fuel.

Preferably, only one side surface of the filter pad is impregnated with fluorescein and, during the step of placing, the filter pad is placed in the chamber with its fluorescein impregnated side surface facing the light sensor. Also, during the step of placing, the filter pad side surfaces are located substantially perpendicular to a line extending between the UV light source and the light sensor. A 300 nm to 500 nm, and more preferably a 400 nm, light bandpass optical filter is provided in the chamber between the UV light source and the filter pad. Additionally, a 500 nm to 650 nm, and more preferably a 550 nm, light bandpass optical filter is provided in the chamber between the filter pad and the light sensor. The UV light source is preferably a 405 nm UV light emitting diode and the light sensor is preferably a silicon photovoltaic diode detector.

A plurality of light sensors can be provided and, during the step of using, the outputs from each of the plurality of light sensors can be averaged for providing the output value representative of the free water present in the hydrocarbon fuel. Alternatively, the light sensor can be a camera and, during the step of using, a digital image output from the camera can be divided into pixel areas, each of the pixel areas can be assigned a weighted value proportional to the light received at that pixel area and the weighted values can then be averaged for providing the output value representative of the free water present in the hydrocarbon fuel.

A receiving slot is also preferably provided through the housing leading to the chamber and, after the step of exposing, the filter pad is secured on a tray and is placed in the chamber by sliding the tray through the receiving slot into the chamber and between the UV light source and the light sensor. The tray includes a pair of arms and each arm has an aligned opening and, during the step of securing the filter pad on the tray, the filter pad side surfaces are aligned with the openings of the arms and a perimeter edge of the filter pad is clamped between the arms. Preferably, an annular recess seat is provided around one arm opening and an annular protruding boss is provided around the other arm opening and, during the step of clamping, the filter pad perimeter edge is placed within the annular recess and the annular boss is received within the annular recess thereby clamping the perimeter edge between the annular recess and the annular boss. After the step of sliding the tray through the receiving slot, the tray effectively closes the receiving slot and prevents ambient light from entering the chamber.

In another form thereof, the present invention is directed to a method of calibrating filter pad reading devices which measure free water in hydrocarbon fuel for use with substantially any test fuel delivery collection method. The method of calibrating a filter pad reading device includes the steps of:
 a. soaking a fluorescein impregnated filter pad with hydrocarbon fuel such as jet engine diesel fuel;
 b. applying a known volume of water on the filter pad at a filter pad reaction area thereby causing the fluorescein to react with the water at the filter pad reaction area;
 c. placing the filter pad in the filter pad reading device;
 d. directing UV light onto the filter pad, measuring the fluorescing light from the filter pad reaction area and recording the filter pad reading device output value;
 e. repeating steps b through d, preferably by applying the known volume of water at different filter pad reaction areas, whereby the recorded filter pad reading device output values are representative of consecutively increasing amounts of reacted fluorescein; and,
 f. calibrating the filter pad reading device by performing data regression of the recorded output values and recording the resulting equation for use by the filter pad reading device in determining the volume of free water on a filter pad which has been exposed to a test volume of the hydrocarbon fuel by passing the fuel through the filter pad.

Preferably, steps b through d are repeated at least nine times for recording output values at least at nine different filter pad reaction areas. The filter pad reaction areas are preferably located on the filter pad in lines forming an "X" pattern.

A filter pad reading device for measuring free water in hydrocarbon fuel which has been calibrated as described can be used with substantially any test fuel delivery collection method by establishing a "collection factor" for each unique delivery collection method. The method for establishing the collection factor for a particular delivery collection method includes the steps of:
 a. combining a known volume of water with a known volume of fuel into a mixture;
 b. using the particular delivery collection method, passing the fuel and water mixture through a fresh filter pad and causing fluorescein on the filter pad to react with the water;
 c. placing the filter pad in the filter pad reading device;
 d. directing UV light onto the filter pad, measuring the fluorescing light from the reacted fluorescein recording the filter pad reading device output value;
 e. repeat steps a through d; and,
 f. establishing the collection factor for the particular delivery collection method by averaging the several filter pad reading device output values and dividing by the known volume of water.

Preferably steps a through d are repeated ten (10) to twenty-five (25) times for obtaining ten (10) to twenty-five (25) filter pad reading device output values, although it is contemplated that these steps could be repeated up to fifty (50) times if needed or desired.

The filter pad reading device which has been calibrated as described can thereafter be used for measuring free water that may be present in fuel and determining acceptable free water contamination levels by using the particular delivery collection method and established collection factor thereof. The method of measuring free water in the fuel includes the steps of:
 a. using a delivery collection method for which a collection factor has previously been established, passing a known volume of the fuel through a fresh filter pad and causing fluorescein on the filter pad to react with free water which may present in the fuel;
 b. placing the filter pad in the filter pad reading device;
 c. directing UV light onto the filter pad, measuring the fluorescing light from the reacted fluorescein and recording the filter pad reading device output value; and,
 d. determining the amount of free water present in the fuel by dividing the filter pad reading device output value by the collection factor and the known volume of fuel.

BRIEF DESCRIPTION OF THE DRAWINGS

The above mentioned and other features and objects of this invention, and the manner of attaining them, will become more apparent and the invention itself will be better understood by reference to the following description of the embodiments of the invention taken in conjunction with the accompanying drawings, wherein.

Figure 1:
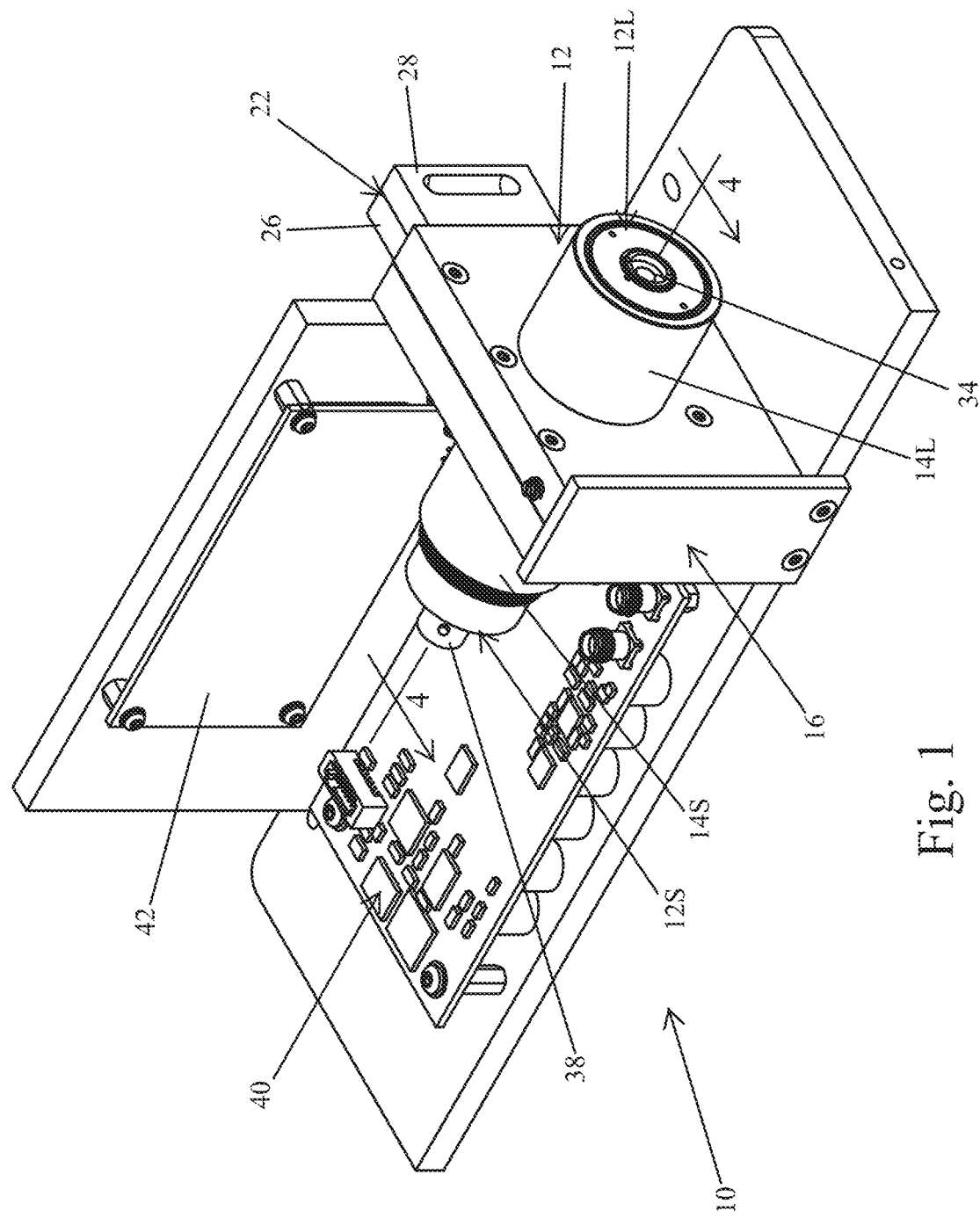
FIG. 1 is a perspective view of an apparatus constructed in accordance with the principles of the present invention for measuring free water in hydrocarbon fuel.

Corresponding reference characters indicate corresponding parts throughout several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION OF THE PREFERRED EMBODIMENTS

An apparatus constructed in accordance with the principles of the present invention for measuring "free water", also known as "undissolved water", levels in hydrocarbon fuels is shown in the drawings and generally designated by the numeral 10. Apparatus 10 includes a housing 12 which defines an interior elongate chamber 14 extending between the housing opposing capped/closed terminal ends 12L and 12S. Housing 12 is formed with a pair of linearly aligned cylindrical tube members 14L and 14S which are mounted on opposite sides of a chassis 16. Chassis 16 can be made as a single integral unit or in two pieces as shown. Chassis 16 includes a cylindrical opening 18 which is aligned with the tube members 14L, 14S. Together, the tube members 14L, 14S and the chassis cylindrical opening 18 form the elongate chamber 14 extending between the housing terminal ends 12L, 12S. Chassis 16 further includes a slide tray receiving slot 20 extending generally perpendicular to and communicating with the chassis opening 18. Receiving slot 20 is adapted to slidingly receive a slide tray 22.

Slide tray 22 is adapted to carry and position a conventional fluorescein coated/impregnated filter pad 24 into the opening 18 of chassis 16. Filter pads 24 are typically made of a relatively thin paper/membrane and are flat disk shaped with a diameter of 0.50 to 1.50 inches. Filter pads 24 hence have opposing generally flat disk shaped side surfaces 24SC, 24SU and a circular perimeter edge 24E. Typically, only one of the side surfaces 24SC is coated/impregnated with fluorescein and the other opposite side 24SU remains uncoated.

Figure 2:
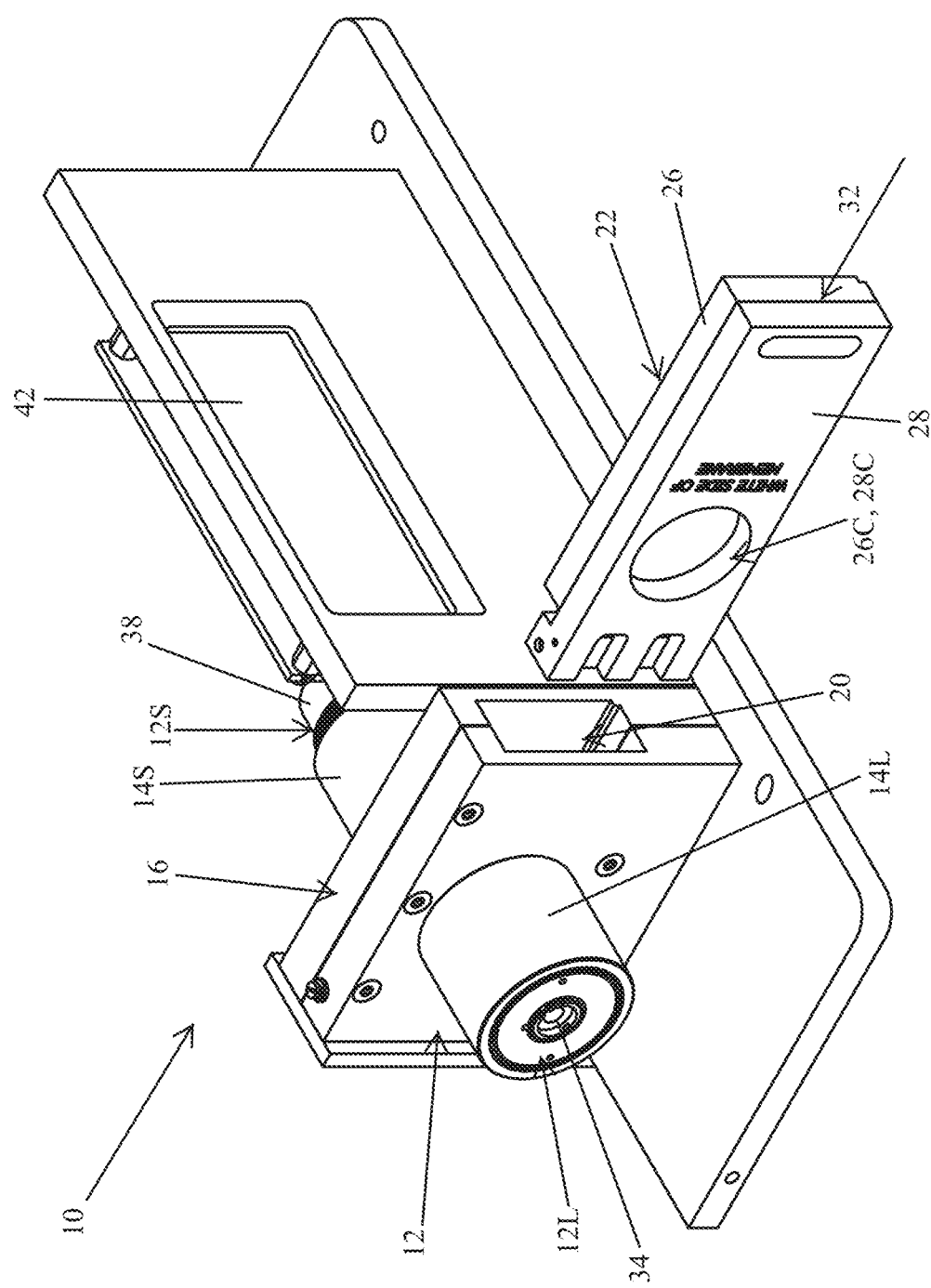
FIG. 2 is another perspective view of the apparatus shown in FIG. 1 and showing the filter pad carrying slide tray adjacent the apparatus slide tray receiving slot.
Figure 3:
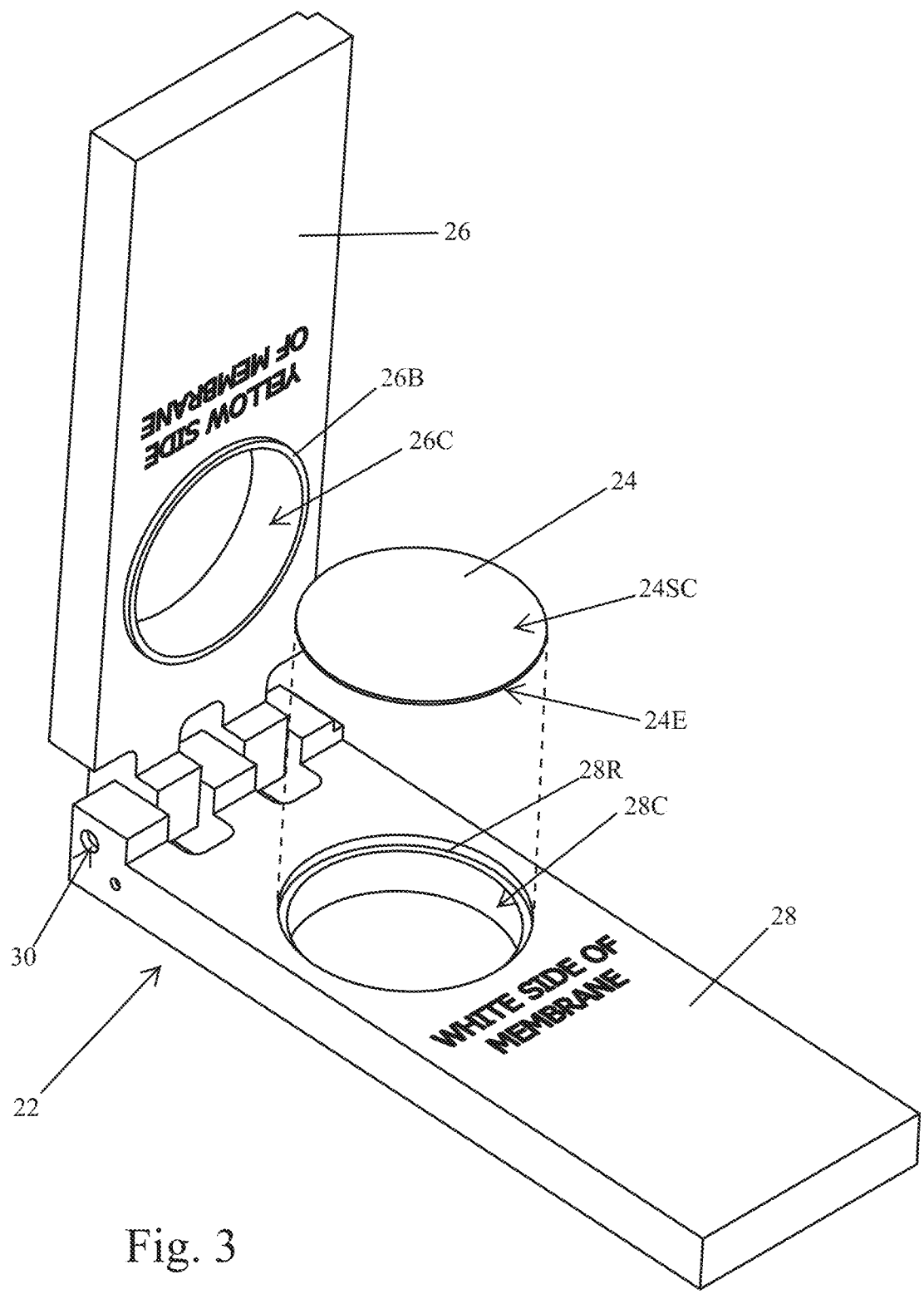
FIG. 3 is a perspective view of the slide tray shown in FIG. 2 in its open position and showing a filter pad which is to be carried by the slide tray into the apparatus receiving slot.

Slide tray 22 comprises a pair of generally flat arms 26, 28. Arms 26, 28 are hingedly connected to one another at pivot joint 30 and are selectively pivotable thereabout between a closed position as shown in FIG. 2 and an open position as shown if FIG. 3. Arms 26, 28 include respective cylindrical openings 26C, 28C which align with one another when the arms 26, 28 are in their closed position. Arm 28 includes an annular recessed seat 28R along the perimeter of its opening 28C. Arm 26 includes an annular protruding boss 26B along the perimeter of its opening 26C. Boss 26B is adapted to be received within the annular recessed seat 28R when the arms 26, 28 are in their closed position. As shown in FIG. 3 and as should now be appreciated, a filter pad 24 is clamped and carried on the slide tray 22 by placing it on the arm 28 with its perimeter edge 24E seated on the recessed seat 28R. The arms 26, 28 are then closed, thereby inserting the protruding boss 26B into the recessed seat 28R and clamping the perimeter edge 24E between the seat 28R and boss 26B. The filter pad 24 is thereby securely retained on the slide tray 22 between the arms cylindrical openings 26C, 28C.

For positioning the filter pad 24 in the opening 18 of chassis 16, the slide tray 22 is inserted into the receiving slot 20 as indicated by arrow 32 and aligning cylindrical openings 26C, 28C thereof with the chassis opening 18. The filter pad 24 is thereby aligned within and positioned generally perpendicular to the elongate chamber 14. The filter pad 24 is further positioned with its coated side surface 24SC facing terminal end 12S and with its uncoated side surface 24SU facing terminal end 12L. When the slide tray 22 is inserted within the receiving slot 20, the receiving slot 20 is effectively closed off thereby preventing light from entering the elongate chamber 14 therethrough.

Figure 4:
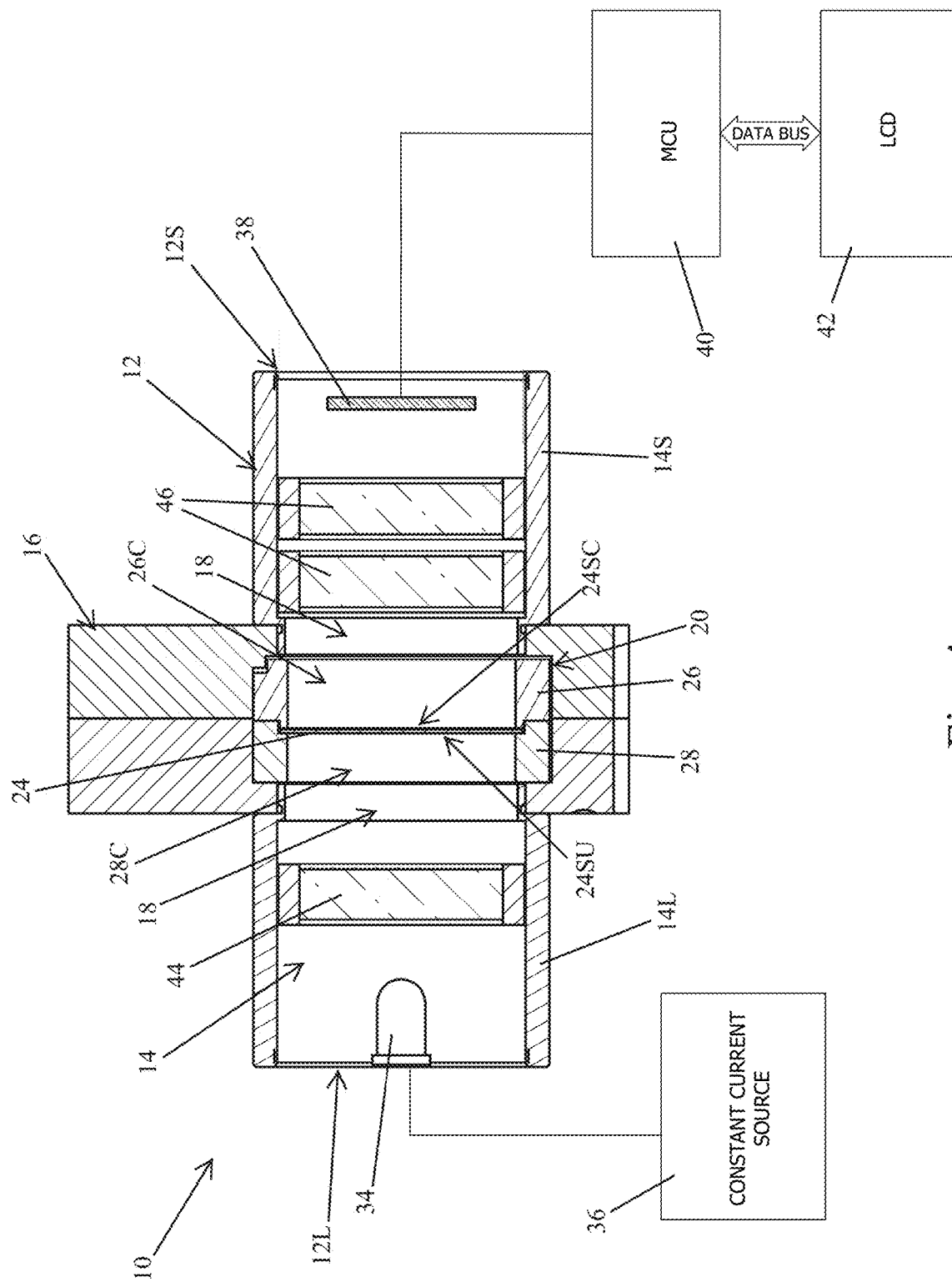
FIG. 4 is a diagramatic cross sectional view of the apparatus shown in FIG. 1 taken along line 4-4 and diagrammatically depicting the electrical connections thereto.
Figure 5:
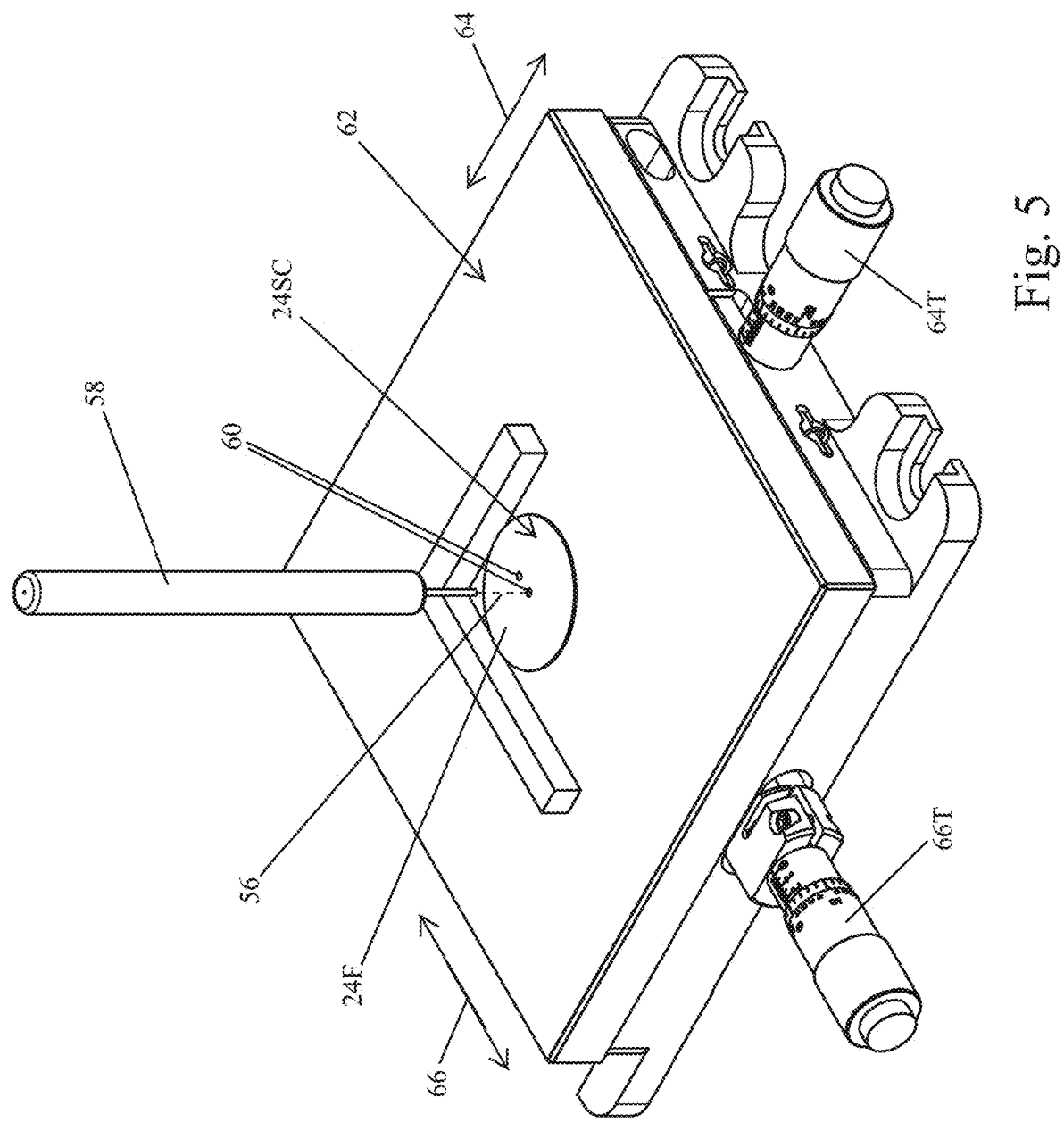
FIG. 5 is a perspective view of a water positioning table that can be used for accurately applying water onto a filter pad which is used for calibrating filter pad reading devices in accordance with the principles of the present invention.

Referring now more particularly to FIG. 4, a UV light emitting diode (UV LED) 34 is provided inside the elongate chamber 14 at the housing terminal end 12L. UV LED 34 is preferably a 405 nm wavelength UV light emitting diode. UV LED 34 is connected to and powered with a stable power/current source 36. A light sensor 38 is provided inside the elongate chamber 14 at the housing terminal end 12S. Light sensor 38 is preferably a silicon photovoltaic diode detector (Si PV Detector). Light sensor 38 is connected to and provides an output current signal (I) to an electronic circuit and microprocessor (MCU) 40. The electronic circuit and MCU 40 convert the output current signal to a digital signal and display a corresponding numeric value on the digital LCD display 42 in a conventional manner.

A UV optical filter/lens 44 is provided between the UV LED 34 and the filter pad 24 for blocking impure sideband transmissions and allowing primarily only the desired UV light bandwidth to travel from the UV LED 34 to the filter pad 24. Preferably, the UV optical filter 44 is a 300 to 500 nm, and most preferably is a 400 nm, wavelength bandpass optical filter. A pair of fluorescing light optical filters/lenses 46 are provided between the filter pad 24 and the light sensor 38 for blocking impure sideband transmissions and allowing primarily only the desired fluorescing light/photon bandwidth to travel from the filter pad 24 to the light sensor 38. Preferably, the fluorescing light optical filters 46 are 500 to 650 nm, and most preferably are 550 nm, wavelength bandpass optical filters.

In operation, for using the apparatus 10, a desired volume of fuel that is to be tested for measuring the free water that may present therein is passed through a fresh/unused filter pad 24. The fuel is passed through the filter pad 24 by directing the fuel onto the filter pad fluorescein coated side surface 24SC and exiting the filter pad uncoated side surface 24SU, so that any free water in the fuel will more readily contact and react with the fluorescein. The fuel is delivered to and through the filter pad 24 using a conventional "delivery collection method" such as, for example, placing the test fuel in a plastic or metal vessel and gravitationally or with a pump delivering the fuel through tubing/piping to the filter pad 24 and forcing the fuel therethrough. After the test fuel is passed through the filter pad 24, thereby exposing the fuel and free water to the fluorescein thereon, the filter pad 24 is placed and clamped in the slide tray 22 as described herein above.

The fluorescing light from the fluorescein on the filter pad 24 which may have reacted with free water in the test fuel is then measured by placing the filter pad 24 into the apparatus 10. To this end, the slide tray 22 is inserted into the chassis receiving slot 20 thereby locating the filter pad 24 in the interior elongate chamber 14 between the light sensor 38 and the UV LED 34 and with its coated side surface 24SC facing the light sensor 38 and its uncoated side 24SU facing the UV LED 34. With the filter pad 24 in the elongate chamber 14, UV light emitted by the UV LED 34 is filtered by the UV optical filter 44 and strikes the filter pad uncoated side surface 24SU. The filter pad paper/membrane is translucent and so the UV light striking the uncoated side surface 24SU travels therethrough to the fluorescein on the coated side surface 24SC. Hence, any fluorescein which reacted with free water is excited by the UV light and fluoresces, thereby emitting fluorescing light/photons. The fluorescing light emitted from the filter pad fluorescein coated side surface 24SC is filtered by the fluorescing light optical filters 46 and strikes the light sensor 38. Advantageously, because the filter pad 24 membrane is translucent, it blocks some of the UV light from traveling therethrough and, with the fluorescing light optical filters 46, the light reaching the light sensor 38 is primarily only fluorescing light from the reacted fluorescein with negligible impure/undesirable side bands. The output current (l) from the light sensor 38 is, therefore, directly proportional to the reacted fluorescein on the filter pad 24 and, hence, can then be used for determining the free water in the test hydrocarbon fuel and determining whether or not the tested fuel contains a sufficiently low/acceptable free water level. In this regard, of course, the output current (l) is converted to a digital signal by the electronic circuit and MCU 40 and a corresponding numeric output value is displayed on the LCD display 42.

Figure 11:
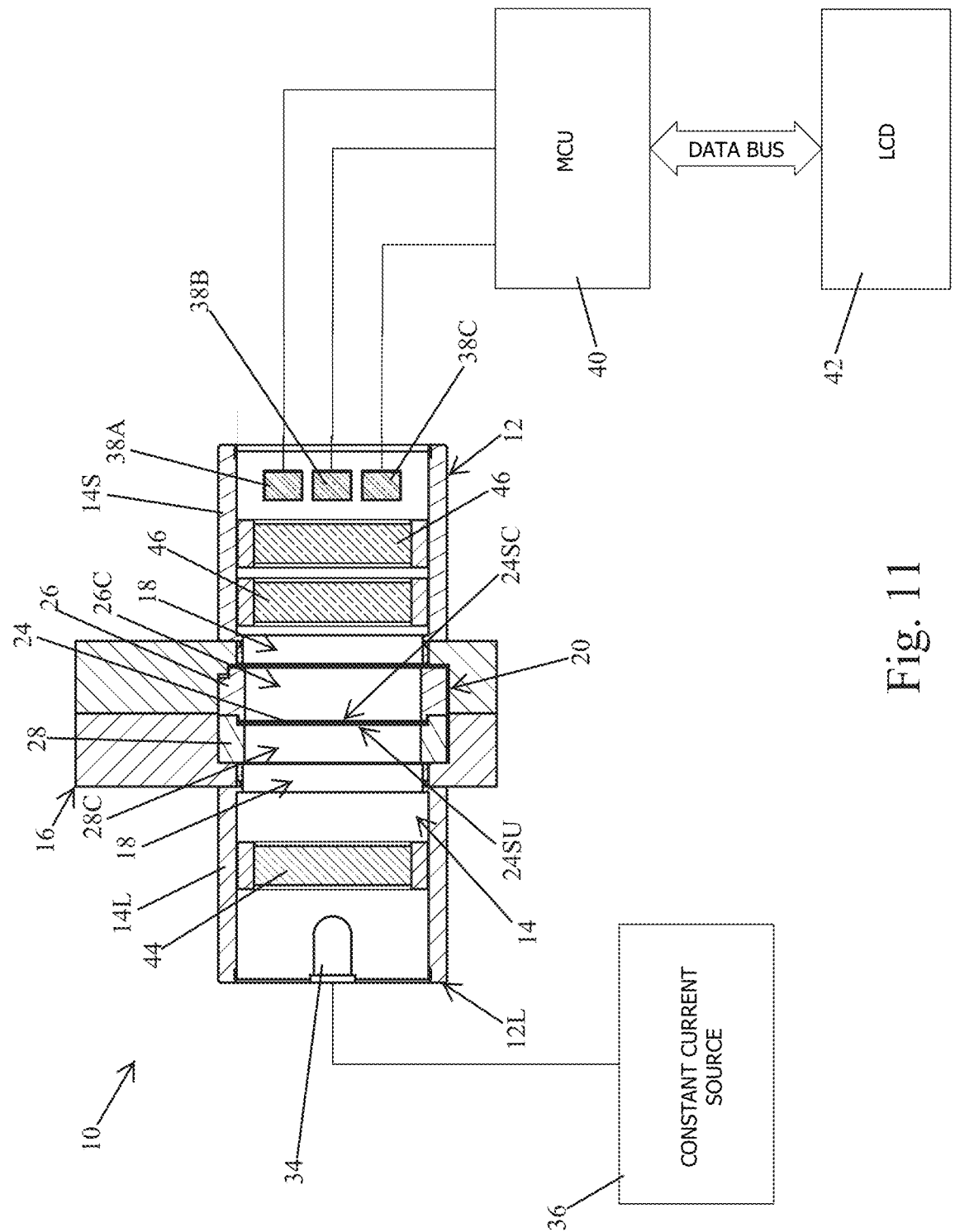
FIG. 11 is a cross sectional view of an apparatus for measuring free water in fuel similar to FIG. 4 but depicting an embodiment which includes a plurality of light sensors that are used to provide an output signal proportional to the reacted fluorescein on the filter pad.

In accordance with the principles of the present invention, the accuracy and reliability of filter pad reading devices is increased, as shown in FIG. 11, by providing a plurality of light sensors 38A, 38B, 38C, etc. Each of the light sensors 38A, 38B, 38C are connected to and provide an output current signal (l) to the electronic circuit and MCU 40. The plurality of output current signals (l) from the sensors 38A, 38B, 38C are then averaged, before or after they are converted to a digital signal, by the electronic circuit and MCU 40, and the resulting numeric output value is displayed on the digital LCD display 42. The resulting numeric output value is, hence, proportional to the reacted fluorescein on the filter pad 24.

Figure 12:
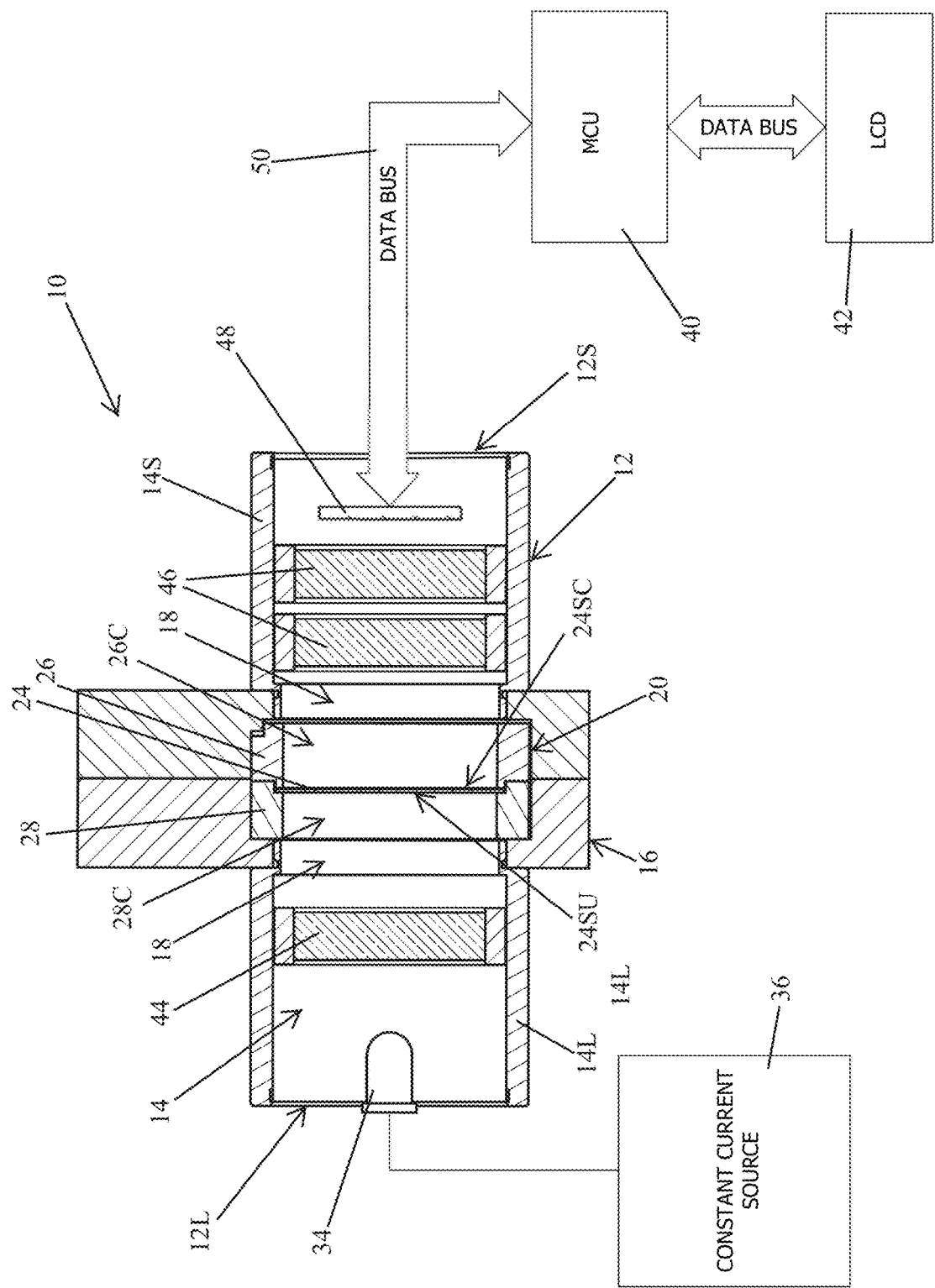
FIG. 12 is a cross sectional view of an apparatus for measuring free water in fuel similar to FIG. 4 but depicting an embodiment which utilizes a digital camera, instead of a light sensor, that is used to provide an output signal proportional to the reacted fluorescein on the filter pad; and, FIG. 13 is a flow chart of a method of measuring free water that may be present in fuel, in accordance with the principles of the present invention, by using a calibrated filter pad reading device utilizing a plurality of light sensors as shown in FIG. 11 or a digital camera as shown in FIG. 12 and a delivery collection method for which a collection factor has previously been established.

In accordance with the principles of the present invention, the accuracy and reliability of filter pad reading devices is further increased, as shown in FIG. 12, by providing a digital camera 48 capable of providing a digital image output through the data bus 50 to the electronic circuit and microprocessor MCU 40. The digital image output from the camera 48 is processed by the electronic circuit and MCU 40 by divided the image into pixel areas and/or individual pixels and assigning weighted values to each of the pixel areas or pixels which are proportional to the fluorescing light received at that pixel area or pixel. The weighted values are then averaged, and the resulting numeric output value is displayed on the digital LCD display 42. The resulting numeric output value is, hence, proportional to the reacted fluorescein on the filter pad 24.

In accordance with the principles of the present invention, the apparatus 10 and/or other filter pad reading devices for measuring free water in hydrocarbon fuel can advantageously be used with substantially any fuel delivery collection method by calibrating the filter pad reading device and, also, establishing a "collection factor" for each unique delivery collection method. Referring now more particularly to FIGS. 5-8, the filter pad reading devices are calibrated by first confirming that the filter pad 24 which is used during calibration does not already contain reacted fluorescein. In this regard, as indicated in the dash line box 52 in the flow chart of FIG. 8, a fresh/unused filter pad 24 is placed into the filter pad reading device and a device output value is obtained/read. This is repeated, if needed, until the device output value is 0.0 microliters, thereby confirming the filter pad 24 does not already contain reacted fluorescein.

After confirming the filter pad 24 does not already contain reacted fluorescein, as indicated in the dash line box 54, it is soaked in a fuel which is known not to contain any free water. The fuel soaked filter pad is shown and designated in the drawings by the numeral 24F. The fuel soaked filter pad 24F hence still does not contain any reacted fluorescein and, if desired, it can be placed into the filter pad reading device to confirm the output value thereof is still 0.0 microliters.

Figure 8:
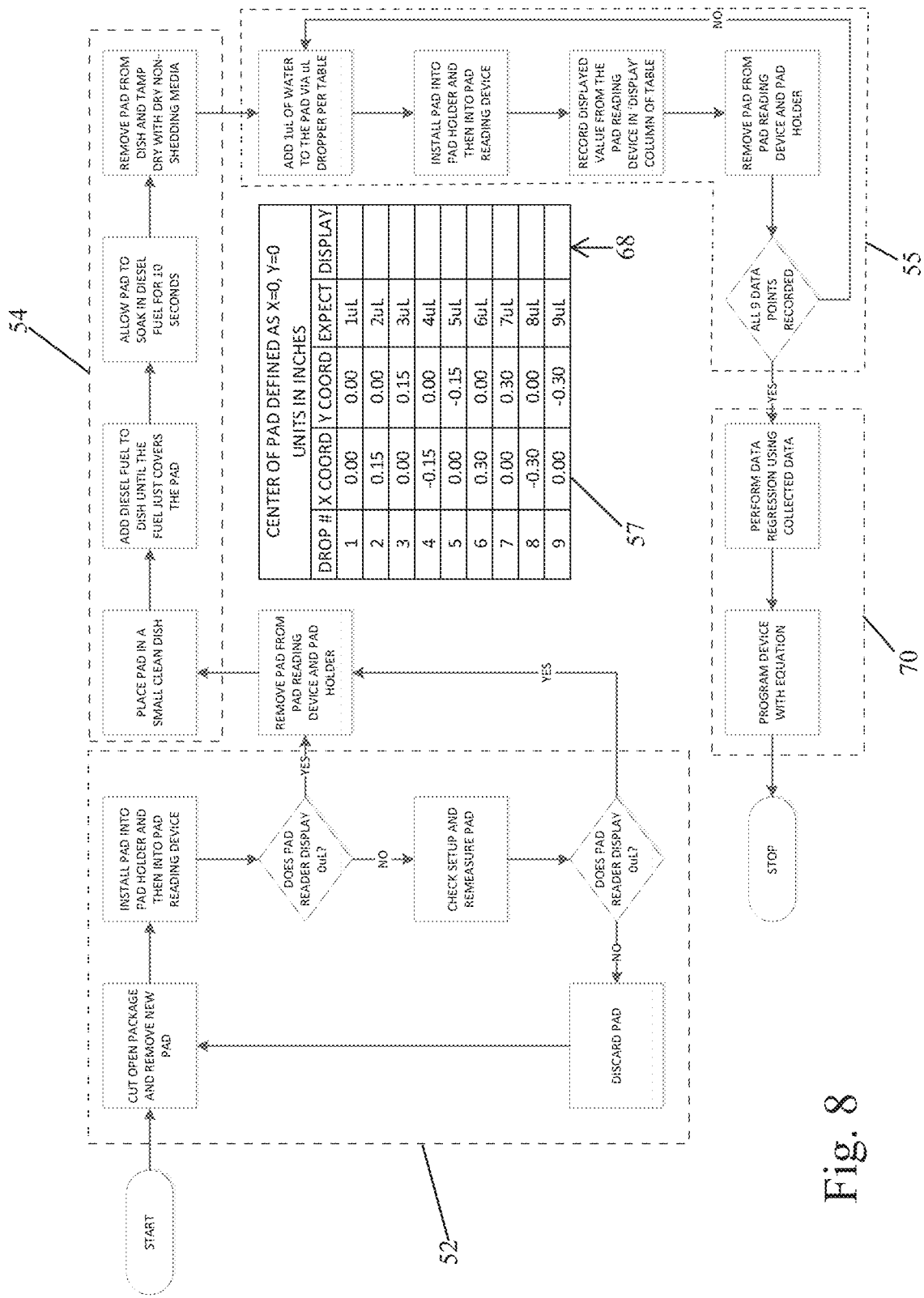
FIG. 8 is a flow chart of the method of calibrating filter pad reading devices which measure free water in hydrocarbon fuel in accordance with the principles of the present invention.

Thereafter, as indicated in the dash line box 55 in the flow chart of FIG. 8, known volume/droplets of water (e.g. 1 microliter) 56 are consecutively placed onto the filter pad 24F thereby creating a consecutively increasing number of fluorescein reaction areas 60 and, after each additional fluorescein reaction area 60 is created, the filter pad 24F is placed into the filter pad reading device and a device output value is obtained/read and recorded. The droplets of water 56, depicted in FIG. 5 by dash line 56, are consecutively applied to the filter pad 24F coated surface 24SC with a syringe or dropper 58 or other means capable of controlling delivery of small quantities of water. When the droplets of water 56 come in contact with the filter pad 24F, they are absorbed and react with the fluorescein, thereby forming filter pad fluorescein reaction areas 60. The droplets of water 56 are preferably placed onto the filter pad 24F at specific different desired locations using, for example, a two axis/ X-Y positioning table 62. The table 62 is moveable as indicated by arrows 64, 66 using the turn knobs 64T, 66T while the syringe 58 remains fixed relative thereto.

Figure 6:
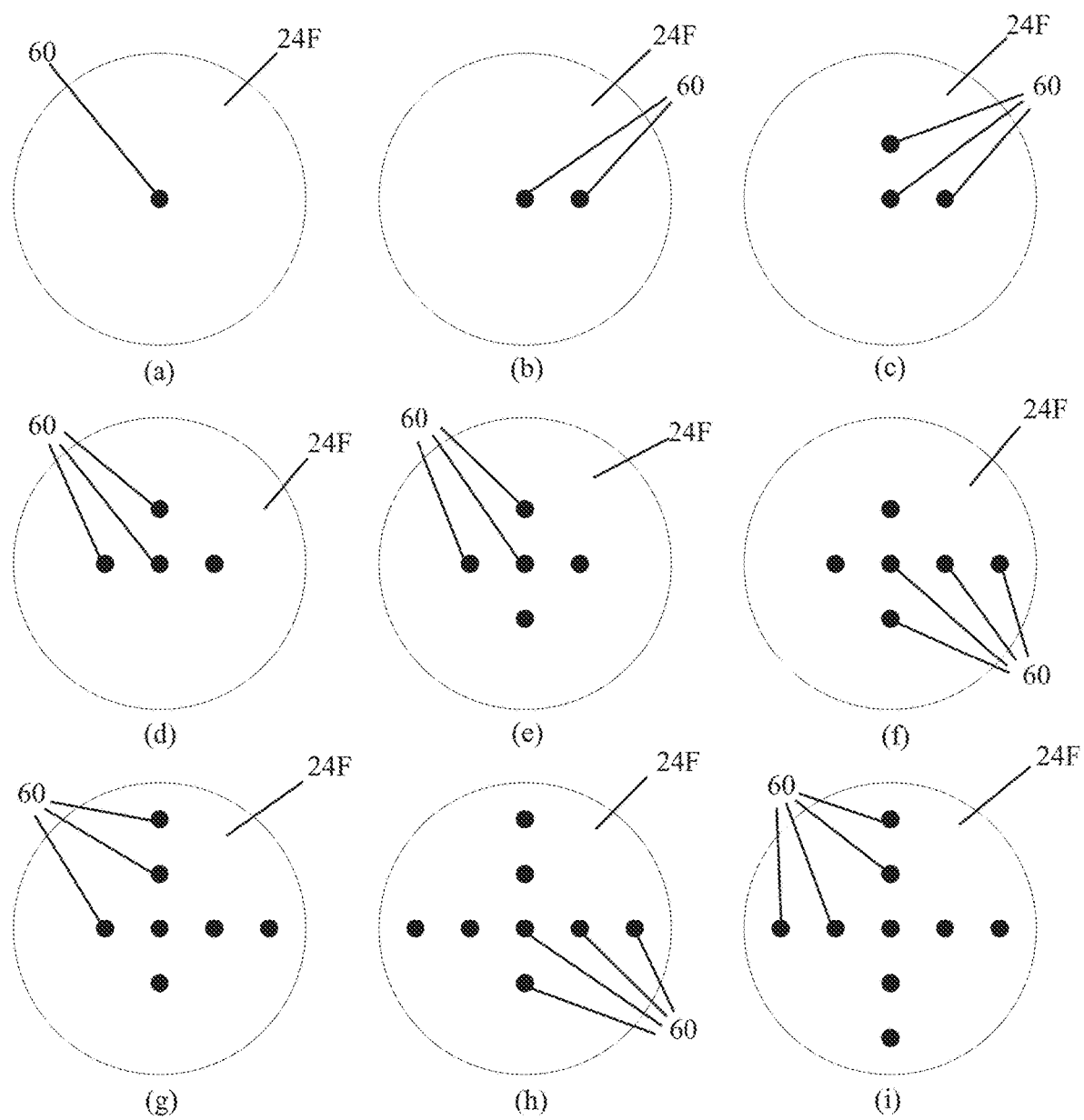
FIG. 6, views (a) through (i), are plan views of a filter pad wherein each view depicts the filter pad with a successive additional droplet/volume of water having been applied using the water positioning table of FIG. 5 for thereby producing fluorescein reaction areas/dots which collectively form an "X" pattern.

Specific different fluorescein reaction areas 60 are thereby consecutively created on the same filter pad 26F, thereby consecutively increasing the total number of reaction areas, as depicted in FIG. 6 wherein each FIG. 6(a)-6(b) depicts the same filter pad 26F after an additional droplet of water 56 has been applied and wherein each dot represents a fluorescein reaction area 60. As also shown in FIGS. 6(a)-6(i), and particularly FIG. 6(i), at least nine individual fluorescein reaction areas 60 are created on the filter pad 24F and, preferably, are placed in lines which together form an "X" pattern.

Figure 7:
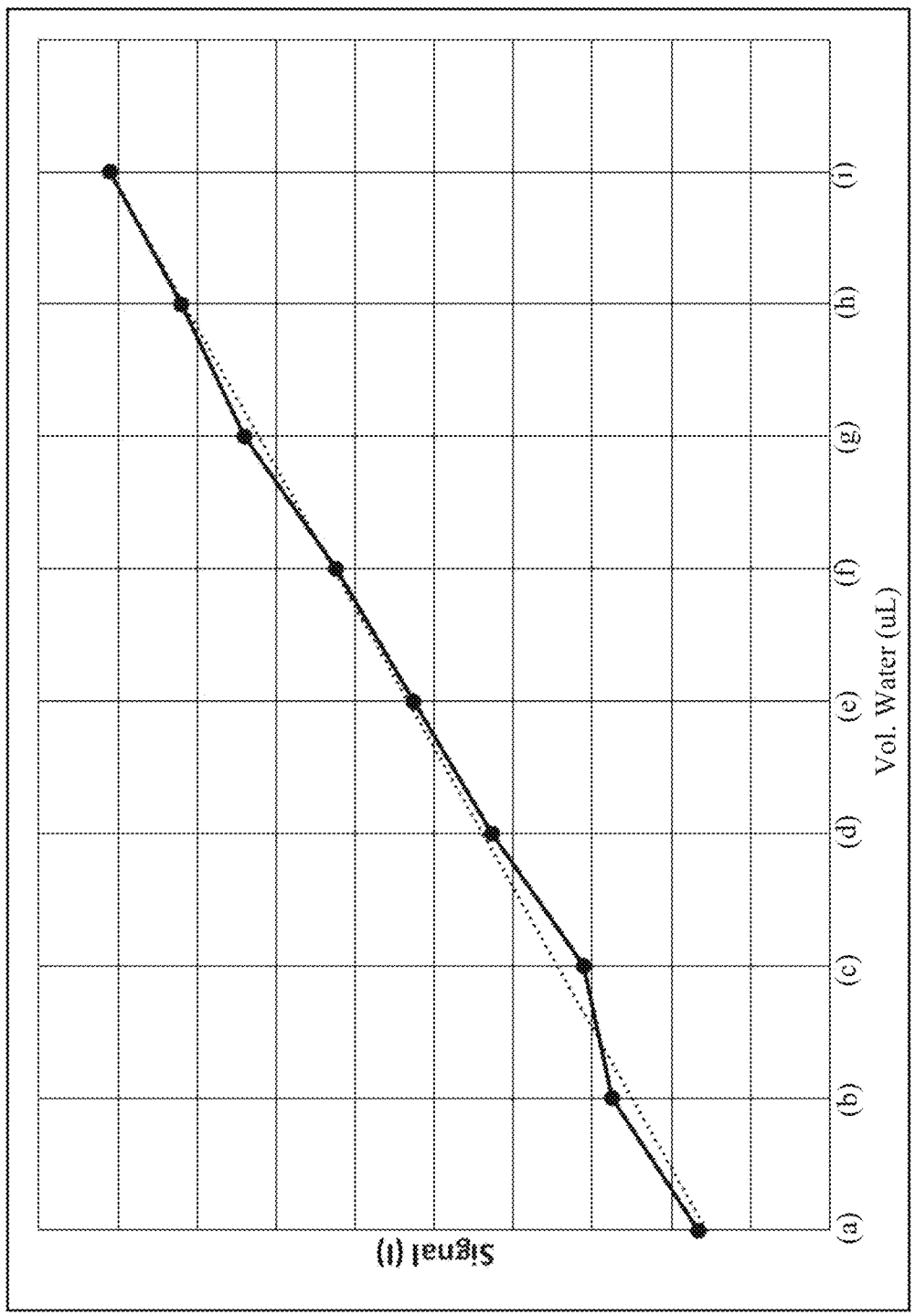
FIG. 7 is a diagrammatic graph depicting the filter pad reading device output values from the successive additional droplets/volume of water applied to the filter pad as shown in FIGS. 6a-6i.

After each fluorescein reaction area 60 is added as depicted by FIGS. 6(a)-6(i), the filter pad 24F is placed into the filter pad reading device and the device output value which is obtained/read is recorded, for example, in the table 57 display/output value column 68. The nine output values/ data points which are thereby recorded in the display column 68 can be plotted as shown in the graph of FIG. 7 wherein, as expected, the output value signal (l) increases as the volume of water/number of fluorescein reaction areas 60 on the filter pad 24F increases.

As finally indicated in the dash line box 70 in the flow chart of FIG. 8, the filter pad reading device is calibrated by performing data regression of the nine recorded output values/data points and recording the resulting equation representative of the FIG. 7 graph for use by the filter pad reading device thereafter in determining the volume of free water on fresh filter pads 24 which have been exposed to a test volume of the hydrocarbon fuel as described hereinabove.

Figure 9:
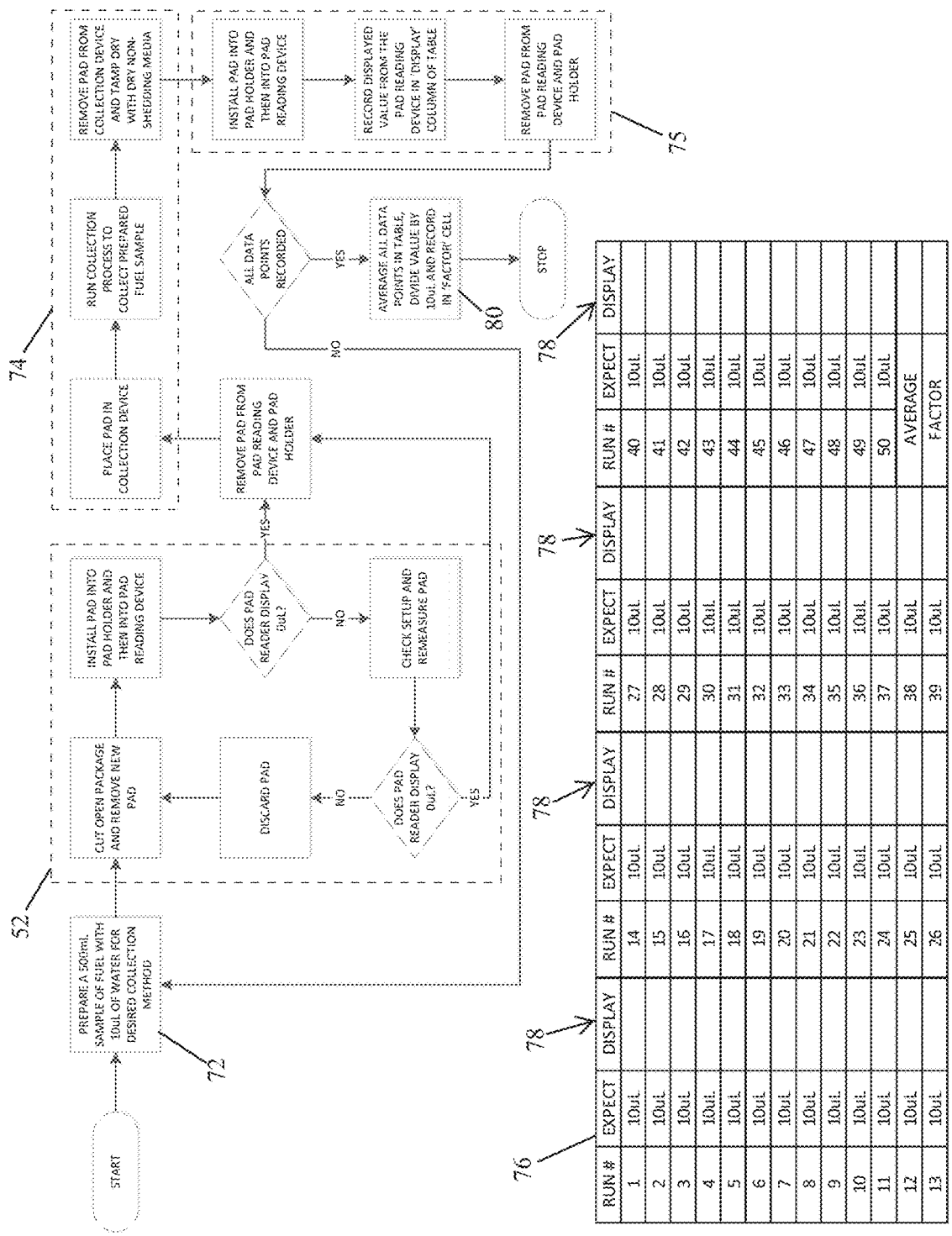
FIG. 9 is a flow chart of a method for establishing a collection factor for each particular delivery collection method that may be used for exposing a filter pad to fuel being tested (by passing a test volume of fuel through the filter pad) and which collection factor may be used with a calibrated filter pad reading device for measuring free water that may be present in the fuel.

A "collection factor" for each unique "delivery collection method" is established, as indicated by the flow chart of FIG. 9. A fuel and water sample is prepared, as indicated by the flow chart box 72, by mixing a known volume of water (10 microliters) with a known volume of fuel (500 microliters) which does not contain any free water. A fresh/unused filter pad 24 is obtained and it is confirmed that it does not already contain reacted fluorescein. In this regard, as indicated in the dash line box 52 in the flow chart of FIG. 9, a fresh/unused filter pad 24 is placed into the filter pad reading device and a device output value is obtained/read. This is repeated, if needed, until the device output value is 0.0 microliters, thereby confirming the filter pad 24 does not already contain reacted fluorescein.

Thereafter, as indicated in the dash line box 74 in the flow chart of FIG. 9, the fuel and water sample is passed through the filter pad 24 using the particular collection method/device thereby exposing the filter pad thereto and causing the fluorescein on the filter pad to react with the known volume of water in the fuel. As then indicated in the dash line box 75, the exposed filter pad is placed into the filter pad reading device and the device output value which is obtained/read is recorded, for example, in the table 76 display/output value column 78. This process of mixing a known volume of water (10 microliters) with a known volume of fuel (500 microliters) which does not contain any free water and preparing a fuel and water sample; passing the fuel and water sample through a fresh/unused filter pad; placing the exposed filter pad into a filter pad reading device and obtaining/reading the device output value; and, recording the output value is repeated a plurality of times and, preferably, at least ten (10) to twenty-five (25) times. In the table 76, this is repeated a total of fifty (50) times as indicated in the "RUN #" columns.

Finally, as indicated in the flow chart box 80, after a desired number of fuel and water sample tests have been run, the output values thereof are averaged, and the average value is divided by the known volume of water (10 microliters) that was used in the fuel and water samples. The result thereof is the "collection factor" for the particular/unique "delivery collection method". The "collection factor" is thereafter used for accurately measuring the volume of free water which may be present in fuel and thereby determining if the fuel contains an acceptable free water contamination level.

Figure 10:
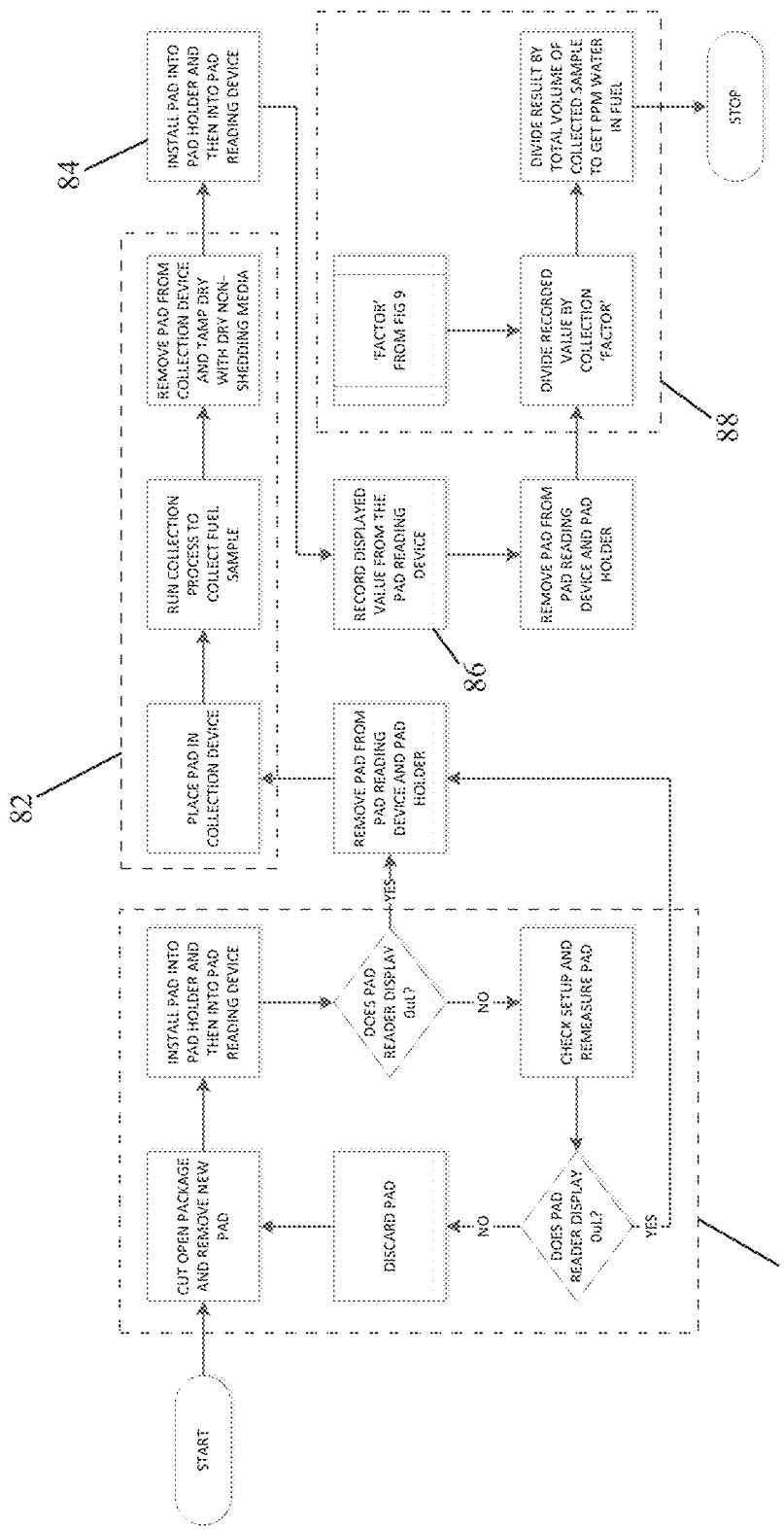
FIG. 10 is a flow chart of a method of measuring free water that may be present in fuel in accordance with the principles of the present invention by using a calibrated filter pad reading device and a delivery collection method for which a collection factor has previously been established.
Figure 13:
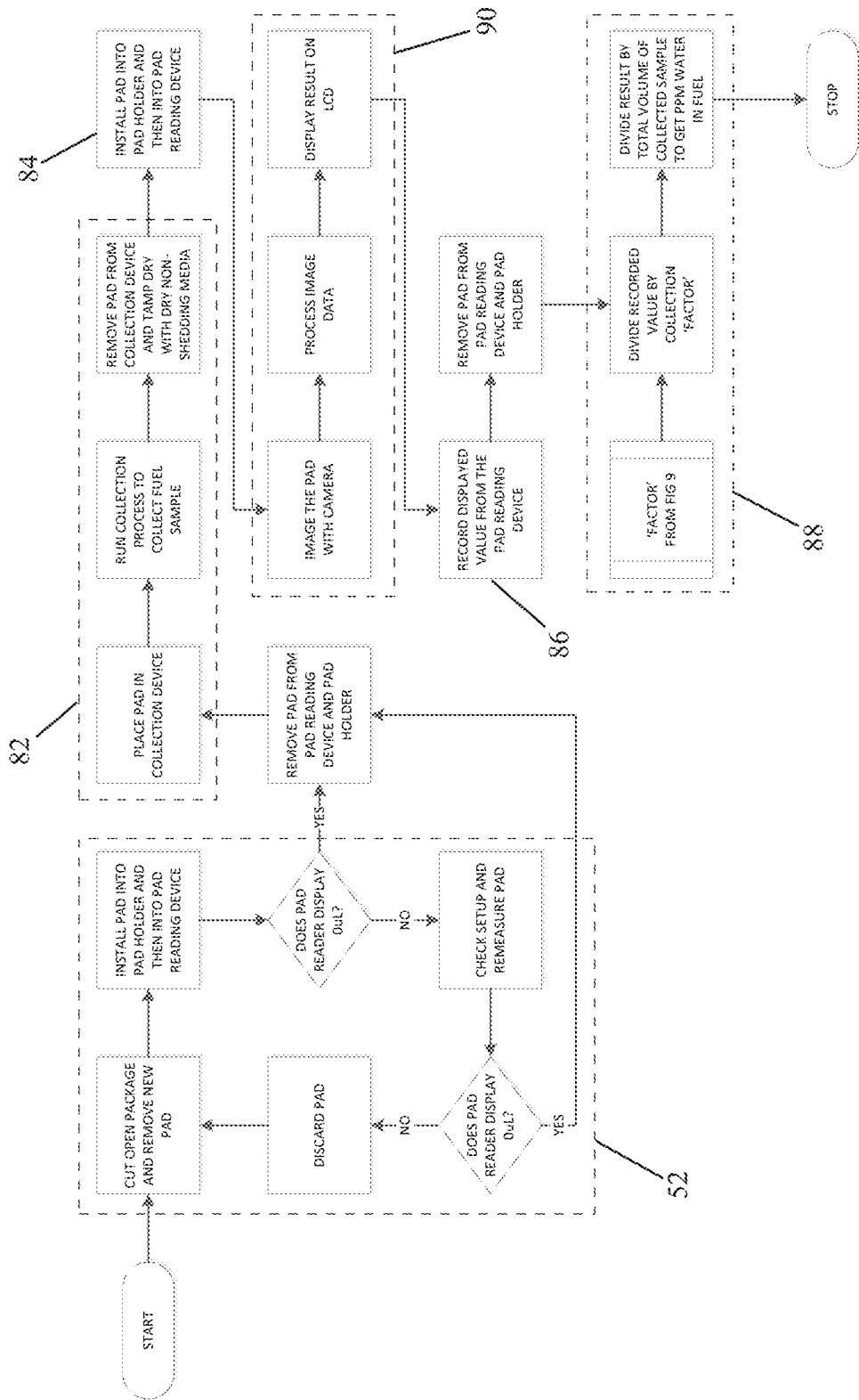

The flow charts of FIGS. 10 and 13 show and describe methods of using filter pad reading devices, such as the apparatus 10 shown in FIGS. 1-4, 11 and 12, which have been calibrated as described hereinabove, for measuring free water in fuel by using a delivery collection method for which a collection factor has previously been established.

FIG. 10 shows and describes a method of using a filter pad reading device, such as the apparatus 10 shown in FIGS. 1-4, which has been calibrated as described hereinabove and which includes a single light sensor 38. As shown in FIG. 10, a fresh/unused filter pad 24 is obtained and it is first confirmed that the filter pad does not already contain reacted fluorescein. In this regard, as indicated in the dash line box 52 in the flow chart of FIG. 10, a fresh/unused filter pad 24 is placed into the filter pad reading device and a device output value is obtained/read. This is repeated, if needed, until the device output value is 0.0 microliters, thereby confirming the filter pad 24 does not already contain reacted fluorescein.

Thereafter, as indicated in the dash line box 82, a known volume of fuel (with an unknown volume of free water) is passed through the filter pad 24 using the particular delivery collection method for which a collection factor was previously been established. The exposed filter pad is then placed into the filter pad reading device such as the apparatus 10 of FIGS. 1-4 and the device output value which is obtained/read (based on the output current signal (I) of sensor 38) is recorded as indicated in the flow chart boxes 84 and 86.

Finally, as indicated in the dash line box 88, the recorded output value is divided by the collection factor of the delivery collection method which was used and also by the volume of the fuel being tested (which was passed through the filter pad). The result thereof is the volume of water in parts per million in the fuel which can then be used for determining whether or not the fuel free water contamination level is acceptable.

FIG. 13 shows and describes a method of using a filter pad reading device, such as the apparatus 10 shown in FIGS. 11 and 12, which have been calibrated as described hereinabove and which include a either a plurality of light sensors 38A, 38B, 38C or a digital camera 48. The method of FIG. 13 is similar to that of FIG. 10 in that it includes the same steps as those of dash line box 52, dash line box 82, flow chart boxes 84, 86 and dash line box 88. Additionally, however, as indicated in the dash line box 90, the current output signals (I) from the sensors 38A, 38B, 38C in the case of the apparatus of FIG. 11 or the weighted values of the pixel areas in the case of the apparatus of FIG. 12, are averaged and the resulting output value therefrom is thereafter used in the method steps of dash line box 88.

While this invention has been described as having an exemplary design, the present invention may be further modified within the spirit and scope of this disclosure. This application is therefore intended to cover any variations, uses, or adaptations of the invention using its general principles.

What is claimed is:

1. A method of measuring free water in hydrocarbon fuel comprising the steps of:
   providing a UV light source, a light sensor and a chamber between the UV light source and the light sensor;
   exposing the hydrocarbon fuel to a fluorescein impregnated filter pad having opposing side surfaces thereby causing free water in the fuel to react with the fluorescein on the filter pad;
   placing the filter pad in the chamber between the UV light source and the light sensor thereby causing UV light from the UV light source to strike one side surface of the filter pad and excite the reacted fluorescein, and causing light emitted from the UV light reacted fluorescein filter pad opposite side surface to strike the light sensor; and,
   using an output from the light sensor to provide an output value representative of the free water present in the hydrocarbon fuel; and,
   wherein the light sensor comprises a camera and wherein, during the step of using, a digital image output from the camera is divided into pixel areas, each of the pixel areas are assigned a weighted value proportional to the light received at that pixel area and the weighted values are then averaged for providing the output value representative of the free water present in the hydrocarbon fuel.

2. The method of claim 1 wherein only one side surface of the filter pad is impregnated with fluorescein and wherein, during the step of placing, the filter pad is placed in the chamber with its fluorescein impregnated side surface facing the light sensor.

3. The method of claim 2 wherein a receiving slot is provided in the chamber and wherein, after the step of exposing, the filter pad is secured on a tray and is placed in the chamber by sliding the tray through the receiving slot into the chamber and between the UV light source and the light sensor.

4. The method of claim 1 wherein, during the step of placing, the filter pad side surfaces are located substantially perpendicular to a line extending between the UV light source and the light sensor.

5. The method of claim 1 further comprising providing a 300 nm to 500 nm light bandpass optical filter in the chamber between the UV light source and the filter pad.

6. The method of claim 1 further comprising providing a 500 nm to 650 nm light bandpass optical filter in the chamber between the filter pad and the light sensor.

7. The method of claim 1 further comprising providing a 400 nm light bandpass optical filter in the chamber between the UV light source and the filter pad.

8. The method of claim 1 further comprising providing a 550 nm light bandpass optical filter in the chamber between the filter pad and the light sensor.

9. The method of claim 1 wherein the UV light source is a 405 nm UV light emitting diode.

10. The method of claim 1 wherein a receiving slot is provided in the chamber and wherein, after the step of exposing, the filter pad is secured on a tray and is placed in the chamber by sliding the tray through the receiving slot into the chamber and between the UV light source and the light sensor.

11. The method of claim 10 wherein, after the step of sliding the tray through the receiving slot, the tray effectively closes the receiving slot and prevents ambient light from entering the chamber.

12. A method of measuring free water in hydrocarbon fuel comprising the steps of:
providing a UV light source, a light sensor and a chamber between the UV light source and the light sensor;
exposing the hydrocarbon fuel to a fluorescein impregnated filter pad having opposing side surfaces thereby causing free water in the fuel to react with the fluorescein on the filter pad;
placing the filter pad in the chamber between the UV light source and the light sensor thereby causing UV light from the UV light source to strike one side surface of the filter pad and excite the reacted fluorescein, and causing light emitted from the UV light reacted fluorescein filter pad opposite side surface to strike the light sensor;
using an output from the light sensor to provide an output value representative of the free water present in the hydrocarbon fuel,
wherein a receiving slot is provided in the chamber and wherein, after the step of exposing, the filter pad is secured on a tray and is placed in the chamber by sliding the tray through the receiving slot into the chamber and between the UV light source and the light sensor; and,
wherein the tray comprises a pair of arms and the arms comprise aligned openings and, during the step of securing the filter pad on the tray, the filter pad side surfaces are aligned with the openings of the arms and a perimeter edge of the filter pad is clamped between the arms.

13. The method of claim 12 wherein the light sensor is a silicon photovoltaic diode detector.

14. The method of claim 12 wherein a plurality of light sensors are provided and, during the step of using, the outputs from each of the plurality of light sensors are averaged for providing the output value representative of the free water present in the hydrocarbon fuel.

15. The method of claim 12 wherein the light sensor comprises a camera.

16. The method of claim 12 wherein the light sensor comprises a camera and wherein, during the step of using, a digital image output from the camera is divided into pixel areas, each of the pixel areas are assigned a weighted value proportional to the light received at that pixel area and the weighted values are then averaged for providing the output value representative of the free water present in the hydrocarbon fuel.

17. The method of claim 12 wherein an annular recess seat is provided around one arm opening and an annular protruding boss is provided around the other arm opening and wherein, during the step clamping, the filter pad perimeter edge is placed within the annular recess and the annular boss is received within the annular recess thereby clamping the perimeter edge between the annular recess and the annular boss.

18. The method of claim 12 wherein only one side surface of the filter pad is impregnated with fluorescein and wherein, during the step of placing, the filter pad is placed in the chamber with its fluorescein impregnated side facing the light sensor and wherein, during the step of placing, the filter pad is placed substantially perpendicular to a line extending between the UV light source and the light sensor.

19. The method of claim 18 further comprising providing a 300 nm to 500 nm light bandpass optical filter in the chamber between the UV light source and the filter pad, and providing a 500 nm to 650 nm light bandpass optical filter in the chamber between the filter pad and the light sensor.

20. A method of measuring free water in hydrocarbon fuel comprising the steps of:
providing a UV light source, a light sensor and a chamber between the UV light source and the light sensor,
exposing the hydrocarbon fuel to a fluorescein impregnated filter pad having opposing side surfaces thereby causing free water in the fuel to react with the fluorescein on the filter pad;
placing the filter pad in the chamber between the UV light source and the light sensor thereby causing UV light from the UV light source to strike one side surface of the filter pad and excite the reacted fluorescein, and causing light emitted from the UV light reacted fluorescein filter pad opposite side surface to strike the light sensor;
using an output from the light sensor to provide an output value representative of the free water present in the hydrocarbon fuel;
wherein only one side surface of the filter pad is impregnated with fluorescein and wherein, during the step of placing, the filter pad is placed in the chamber with its fluorescein impregnated side facing the light sensor and wherein, during the step of placing, the filter pad is placed substantially perpendicular to a line extending between the UV light source and the light sensor;

further comprising providing a 300 nm to 500 nm light bandpass optical filter in the chamber between the UV light source and the filter pad, and providing a 500 nm to 650 nm light bandpass optical filter in the chamber between the filter pad and the light sensor, wherein a receiving slot is provided in the chamber and wherein, after the step of exposing, the filter pad is secured on a tray and is placed in the chamber by sliding the tray through the receiving slot into the chamber and between the UV light source and the light sensor; and, wherein, after the step of sliding the tray through the receiving slot, the tray effectively closes the receiving slot and prevents ambient light from entering the chamber.

\* \* \* \* \*